United States Patent [19]

Hoffman et al.

[11] Patent Number: 5,066,336
[45] Date of Patent: Nov. 19, 1991

[54] METHOD FOR CLEANING REAGENT DELIVERY PROBES

[75] Inventors: Julie F. Hoffman, Durham, N.C.; Lionel D. Jones, II, Ventura, Calif.

[73] Assignee: Akzo N.V., Arnhem, Netherlands

[21] Appl. No.: 588,168

[22] Filed: Sep. 29, 1990

Related U.S. Application Data

[62] Division of Ser. No. 443,954, Dec. 1, 1989, Pat. No. 4,989,623.

[51] Int. Cl.$^5$ .......................... B08B 9/00; B08B 9/02; B08B 9/06
[52] U.S. Cl. ............................. 134/22.12; 134/22.13; 134/22.18; 134/28; 134/29; 134/61; 134/76; 134/83; 134/88; 134/89; 134/95; 134/169 R; 134/170; 141/90; 141/91; 73/864.22; 422/33; 422/39
[58] Field of Search ..................... 134/22.12, 22.13, 28, 134/29, 61, 76, 83, 88, 89, 95, 169 R, 170, 22.18; 73/864.22; 141/90, 91; 422/33, 39

[56] References Cited

U.S. PATENT DOCUMENTS 4,434,672 3/1984 Williamson et al. ............. 73/864.22
4,817,443 4/1989 Champseix et al. ................... 141/91

OTHER PUBLICATIONS

McCoy et al., Quality Control in Flow Cytometry for Diagnostic Pathology, Quality Control in Flow Cytometry, vol. 93, No. 4, Apr. 1990, p. 531.

Primary Examiner—Theodore Morris
Assistant Examiner—Zeinab El-Arini
Attorney, Agent, or Firm—Spencer & Frank

[57] ABSTRACT

A cleaning apparatus for cleaning delivery probes used for dispensing protein-containing reagents. The apparatus includes: a bath of a cleaning solution for a protein-containing reagent; a device for lowering the probe into the cleaning solution for aspirating cleaning solution into the probe and for coating the outside of the probe; a device for raising the probe from the cleaning solution; a device for forcing primer liquid through the probe for expelling aspirated cleaning solution followed by primer liquid from the probe for washing the inside of the probe; and a device for deflecting cleaning solution and primer liquid expelled from the probe onto the outside of the probe for washing the outside of the probe.

11 Claims, 3 Drawing Sheets

METHOD FOR CLEANING REAGENT DELIVERY PROBES

This is a division of application Ser. No. 07/443,954 filed Dec. 1st, 1989 now U.S. Pat. No. 4,989,623.

BACKGROUND OF THE INVENTION

The present invention relates to a process of cleaning a reagent delivery probe and an apparatus for practicing the process.

A problem in automatic delivery systems for protein-containing reagents has been that each reagent requires a separate probe to deliver the reagent to the reaction mixture. Such a system is described in co-pending and concurrently filed U.S. patent application No. 07/443,951 to Karp et al. which is commonly owned by the assignee of the present application, the entire disclosure of which is hereby incorporated by reference. Particularly in the case of clotting proteins such as thrombin, cleaning the probe is so difficult that using a single probe to deliver thrombin and another reagent to a reaction mixture has not been commercially successful. Further, because thrombin is prone to adhere to the probe it is delivered from as it dries, even if thrombin is the only reagent delivered from a probe, there may be problems in keeping the probe clean.

SUMMARY OF THE INVENTION

Therefore, it is an object of the present invention to provide a method and apparatus for cleaning a probe used to dispense protein-containing reagents which allow the probe to be used to dispense more than one reagent.

The above and other objects are achieved in accordance with one aspect of the invention by the provision of a cleaning apparatus for a hollow delivery probe which is used repeatedly in an automatic system for dispensing protein-containing reagents comprising: a bath of a cleaning solution for a protein-containing reagent; a device for lowering the probe into the cleaning solution for aspirating cleaning solution into the probe and to coat the outside of the probe; a device for raising the probe from the cleaning solution; a device for forcing primer liquid through the probe for expelling aspirated cleaning solution followed by primer liquid from the probe for washing the inside of the probe; and a device for deflecting cleaning solution and primer liquid expelled from the probe onto the outside of the probe for washing the outside of the probe.

In a further aspect of the invention there is also provided a process for cleaning a hollow delivery probes which is repeatedly used in an automatic system for dispensing protein-containing reagents comprising the steps of: lowering the probe, contaminated with a protein-containing reagent, in a cleaning solution for removing protein-containing reagents; aspirating the cleaning solution into the probe and coating the cleaning solution on the outside of the probe; raising the probe from the cleaning solution; forcing a primer liquid through the probe to expel the aspirated cleaning solution followed by primer liquid from the probe to clean the inside of the probe; and deflecting the expelled cleaning solution primer liquid onto the outside of the probe to clean the outside of the probe

DESCRIPTION OF THE PREFERRED EMBODIMENTS

Figure 1:
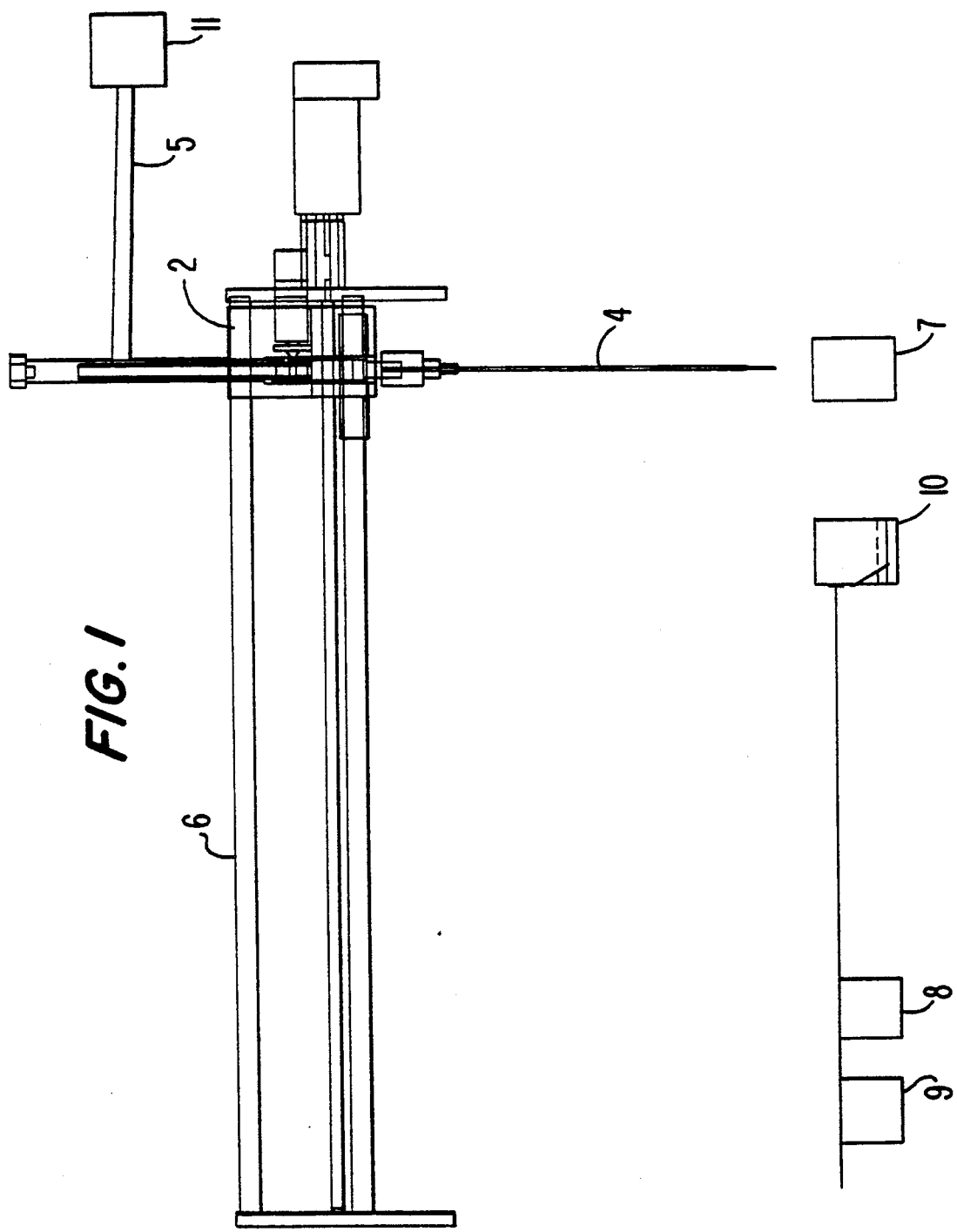
FIG. 1 is a schematic diagram of a probe type reagent dispensing system employing a cleaning apparatus according to one embodiment of the invention.

FIG. 1 illustrates a protein-containing reagent dispensing device 2 having a pipette or hollow probe 4 for dispensing a protein-containing reagent, such as thromboplastin, thrombin, etc. Dispensing device 2 may be moved horizontally along a track 6, which may be a horizontal lead screw, or up and down along a vertical lead screw. During operation, probe 4 is lowered into a reagent container 8 to aspirate a first reagent into probe by means of a displacement pump 5 controlled by a controller 11. Probe 4 is then moved over a reaction vessel 7 and is lowered into reaction vessel 7 so that reagent can be dispensed into reaction vessel 7 by forcing air or a primer liquid such as water through probe 4 by means of displacement pump 5. After a first reagent is dispensed into reaction vessel 7, probe 4 is cleaned both inside and outside at a wash station 10. After being cleaned, probe 4 may aspirate a second reagent in a second container 9. After dispensing the second reagent into reaction vessel 7, probe 4 is again cleaned at wash station 10 so that another reagent may again be aspirated.

Figure 2:
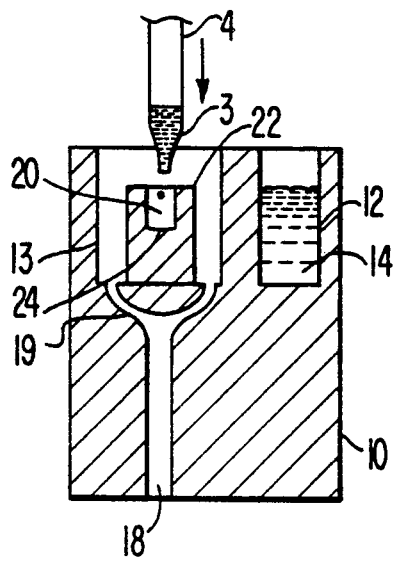
FIG. 2 is a sectional view of part of the apparatus of FIG. 1 during one sequence of the cleaning process according to the invention.
Figure 3:
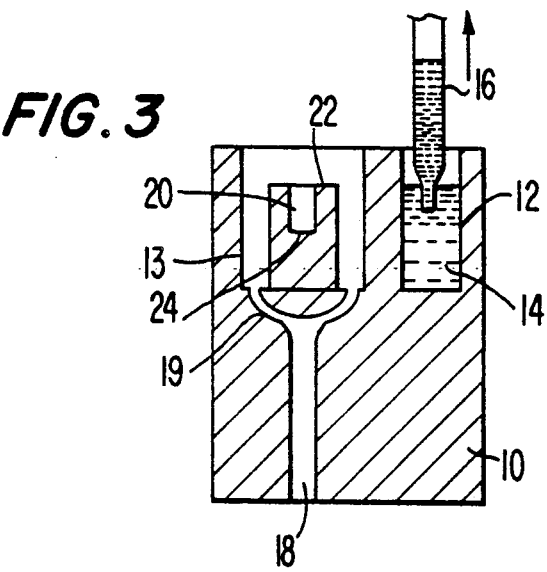
FIG. 3 is another sectional view of part of the apparatus of FIG. 1 during another sequence of the cleaning process according to the invention.
Figure 4:
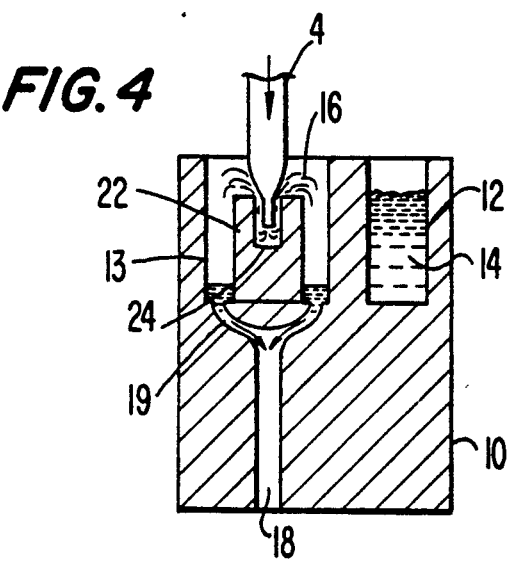
FIG. 4 is another sectional view of part of the apparatus of FIG. 1 during another sequence of the cleaning process according to the invention.

A first embodiment of the invention is illustrated in detail in FIGS. 2, 3 and 4. As shown in FIG. 2, residual protein-containing reagent 3 is preferably expelled from probe 4 prior to aspirating cleaning solution 14 from cleaning solution bath 12. After expelling residual reagent into a recess 20, having a bottom 24 and located in a trough 13, probe 4 is moved to a position shown in FIG. 3 and lowered into cleaning solution bath 12. Cleaning solution 16 is then aspirated into probe 4. Probe 4 is then raised and moved to a position above recess 20. Probe 4 is then lowered until it is surrounded by walls 22 of recess 20. Cleaning solution is then forced through probe 4 by means of a primer liquid injected into probe. A preferred primer liquid is water. As the primer flows through probe 4, cleaning solution is expelled and the primer liquid washes remaining cleaning solution from the inside of probe 4. Following expulsion of the cleaning solution, primer liquid is additionally expelled from probe 4. The cleaning solution deflected by bottom 24 of recess 20 forms a fountain which washes the outside of probe 4, first with cleaning solution and then with primer liquid to clean the outside of probe. After cleaning, probe 4 is then ready to aspirate another reagent. Waste cleaning solution and primer liquid are drained from trough 13 by means of drainage passages 19 which connect to a drainage bore 18. While drainage passages 19 are illustrated as being located at the location of recess 20, drainage passages may be located throughout the bottom of trough 13.

While any solution suitable for breaking down protein-containing reagents may be used as the cleaning solution, for probes used to dispense thrombin, a preferred cleaning solution is a bleach (sodium hypochlorite) solution, preferably a 10% bleach solution. Further, when a 10% bleach solution is the cleaning solution, the amount of bleach solution used is preferably about half of the amount of reagent delivered. The amount of water forced through the probe is preferably about 10 times the amount of bleach solution used.

Figure 5:
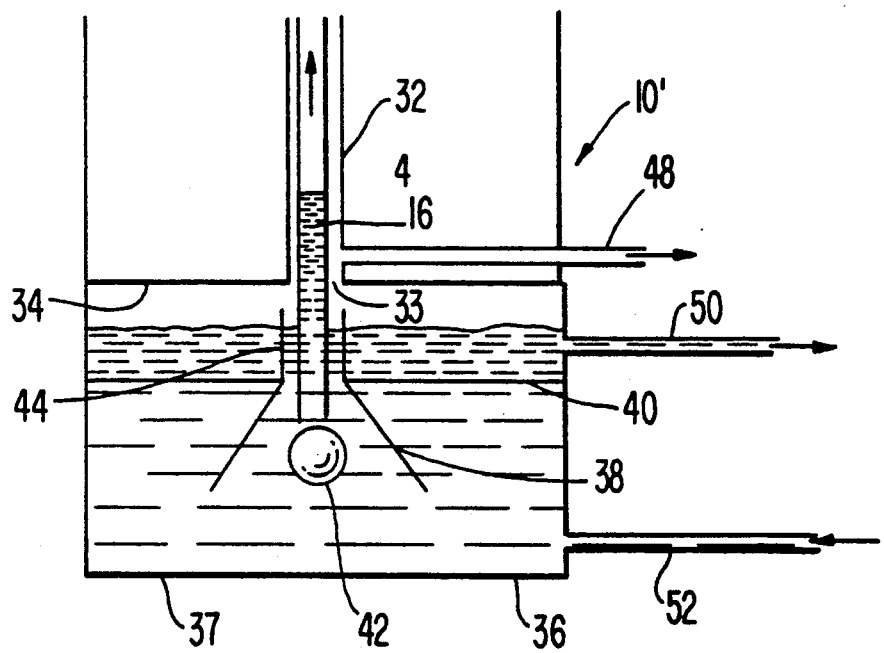
FIG. 5 is a sectional view of another embodiment of the invention during a sequence of the cleaning process according to the invention.
Figure 6:
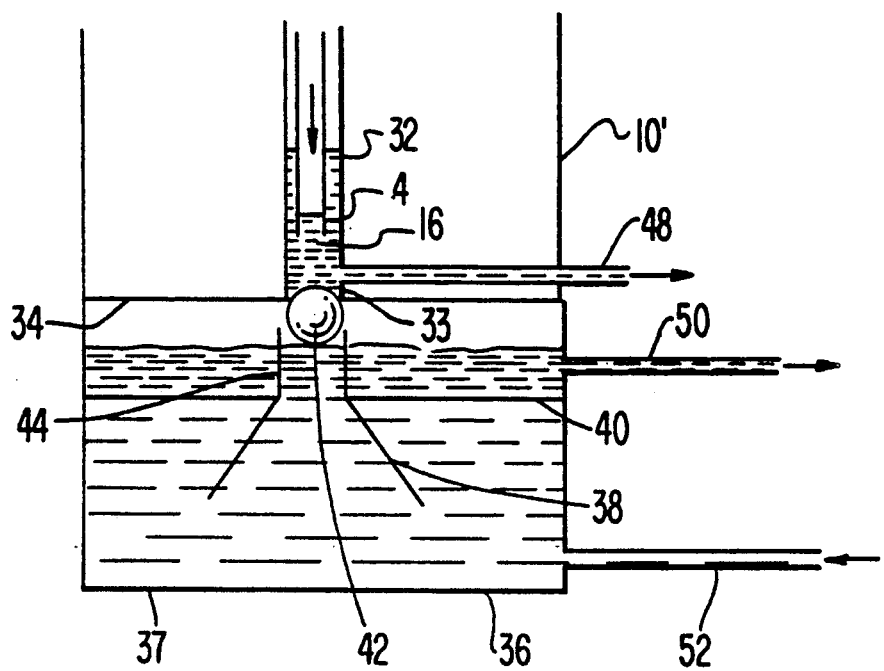
FIG. 6 is another sectional view of the embodiment of the invention shown in FIG. 5 during another sequence in the cleaning process.

FIGS. 5 and 6 illustrate a second embodiment of the invention which provides a modified wash station 10'. The remaining parts of the apparatus are identical to those illustrated in FIG. 1 and their functions are described above.

In FIG. 5, probe 4 is lowered into wash station 10' through a passage 32 which passes through the top 34 of a container 37 which contains a bath 36 of cleaning solution. At the bottom of passage 32 is an opening 33. As probe 4 is lowered, the end of probe 4 dislodges a ball 42 from an opening 44, which in the embodiment shown is a cylindrical passage. When probe 4 has displaced ball 42 to the point where opening 44 widens into an inverted frustoconical passage 38, cleaning solution 16 from bath 36 of cleaning solution is able to pass around ball 42 and be aspirated into probe 4. Frustoconical passage 38 acts to constrain the movement of ball 42 so that it will follow probe 4 up as probed 4 is raised. Frustoconical passage 38 is supported in place by means of support members 40 and may consist of separate bent vertical strips with spaces between the strips or may be a unitary cone.

As shown in FIG. 6, when probe 4 is raised, ball 42 follows probe 4 upwardly until it is floating on top of the cleaning solution and abuts an edge of passage 32, thereby closing opening 33 of passage 32, because ball 42 is larger in diameter than opening 33. Primer liquid is then forced through probe 4, thereby expelling cleaning solution from probe 4 and cleaning the inside of probe. As the cleaning solution and the primer liquid are expelled from probe 4, they are deflected upwardly by ball 42 and thereby cleaning the outside of probe 4. A tube 48 drains waste liquid from the area on top of ball 42 and may be connected to a suction pump.

The level of cleaning solution in bath 36 is maintained by means of an inflow pipe 52 and an outflow pipe 50.

The following example illustrates an embodiment of the invention:

EXAMPLE

A probe was used to aspirate approximately 66 μl of thrombin from a reservoir. The thrombin was then delivered to a cuvette. Next, the probe was moved over a bleach reservoir and lowered into the reservoir to pipette 35 μl of a 10% solution of bleach into the probe. The probe was then moved over a deflection recess and lowered into the recess. Finally, approximately 300 μl of water was forced through the probe to clear bleach and reagent from the inside of the probe and to cause bleach and water to fountain over the outside of the probe to clean the outside of the probe.

It will be understood that the above description of the present invention is susceptible to various modifications, changes and adaptations, and the same are intended to be comprehended within the meaning and range of equivalents of the appended claims.

What is claimed is:

1. A process for cleaning a hollow delivery probe, used in a sample handling system, said probe having a free end, said process comprising:

forcing a cleaning solution through at least a portion of the probe to expel the cleaning solution from the free open end of the probe; and deflecting the expelled cleaning solution onto the outside of the probe by directing the expelled cleaning solution into a recess having a closed bottom and which is shaped for creating a fountain of the expelled cleaning solution wherein the deflected amount is sufficient to clean the outside of the probe.

2. The process of claim 1, wherein said cleaning solution comprises bleach.

3. The process of claim 1, wherein said cleaning solution comprises about 10% bleach.

4. The process of claim 1, further including aspirating the cleaning solution into the probe from the free open end prior to said forcing step.

5. The process of claim 4, wherein said aspirating step is performed at a first probe position and said deflecting step is performed at a second probe position and said process further comprises the step of moving the probe from the first position to the second position.

6. The process of claim 1, further comprising the step of collecting and draining waste cleaning solution for disposal.

7. A process for cleaning a hollow delivery probe, used in a sample handling system, said probe having a free end, said process comprising:

forcing a cleaning solution through at least a portion of the probe to expel the cleaning solution from the free open end of the probe;

deflecting the expelled cleaning solution onto the outside of the probe to clean the outside of the probe;

forcing a primer liquid through the probe following the cleaning solution so as to expel remaining cleaning solution and primer liquid from the probe; and deflecting the expelled remaining cleaning solution and primer liquid onto the outside of the probe to clean the outside of the probe.

8. The process of claim 7, wherein said primer liquid comprises water.

9. The process of claim 7, wherein about 10 μl of primer liquid is forced through the probe for every 1 μl of cleaning solution forced through the probe.

10. A process for cleaning a hollow delivery probe, used in a sample handling system, said probe having a free end, said process comprising:

forcing a cleaning solution through at least a portion of the probe to expel the cleaning solution from the free open end of the probe;

deflecting the expelled cleaning solution onto the outside of the probe to clean the outside of the probe; and lowering the probe into a bath of cleaning solution and aspirating the cleaning solution into the probe and coating the cleaning solution on the outside of the probe.

11. The process of claim 10, wherein the bath is enclosed in a container including a top located above said cleaning solution, the top defining an opening for allowing the probe to be lowered into the cleaning solution, the container including means defining an inverted frustoconical passage disposed in the cleaning solution and communicating with the opening, the container housing a ball which floats on the cleaning solution for closing said opening, the ball being constrained by the frustoconical passage means and being downwardly displaceable by the probe when the probe is lowered into the cleaning solution to allow cleaning solution to be aspirated into the probe and wherein said lowering step further comprises displacing into the cleaning solution the ball which closes the container containing the bath of cleaning solution, thereby allowing cleaning solution to be aspirated into the probe and said deflecting step comprises deflecting expelled cleaning solution by the ball which closes the container after the probe is raised.

* * * * *